US00PP33911P2

(12) United States Plant Patent
Koppe

(10) Patent No.: US PP33,911 P2
(45) Date of Patent: Jan. 25, 2022

(54) ***BEGONIA* PLANT NAMED 'KRBETWH01'**

(50) Latin Name: ***Begonia* x *hiemalis***
Varietal Denomination: KRBETWH01

(71) Applicant: Lubbertus H. Koppe, Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 0 days.

(21) Appl. No.: 17/339,875

(22) Filed: Jun. 4, 2021

(51) Int. Cl.
*A01H 5/02* (2018.01)
*A01H 6/18* (2018.01)

(52) U.S. Cl.
USPC ..... Plt./345
CPC ..... *A01H 6/185* (2018.05)

(58) Field of Classification Search
USPC ..... Plt./345
CPC ..... A01H 6/185
See application file for complete search history.

(56) References Cited

PUBLICATIONS

UPOV hit on *Begonia* plant named, 'KRBETWH01', QZ PBR 2020/2762, filed Nov. 4, 2020.*

* cited by examiner

*Primary Examiner* — Anne Marie Grunberg
(74) *Attorney, Agent, or Firm* — C. Anne Whealy

(57) ABSTRACT

A new and distinct cultivar of *Begonia* plant named 'KRBETWH01' characterized by its broadly upright and mounded plant habit; moderately vigorous to vigorous growth habit; moderately freely branching habit; dark green-colored leaves; freely flowering habit; semi-double and double-type male flowers that are white in color and held above and beyond the foliar plane; and good postproduction longevity.

2 Drawing Sheets

Figure 1:
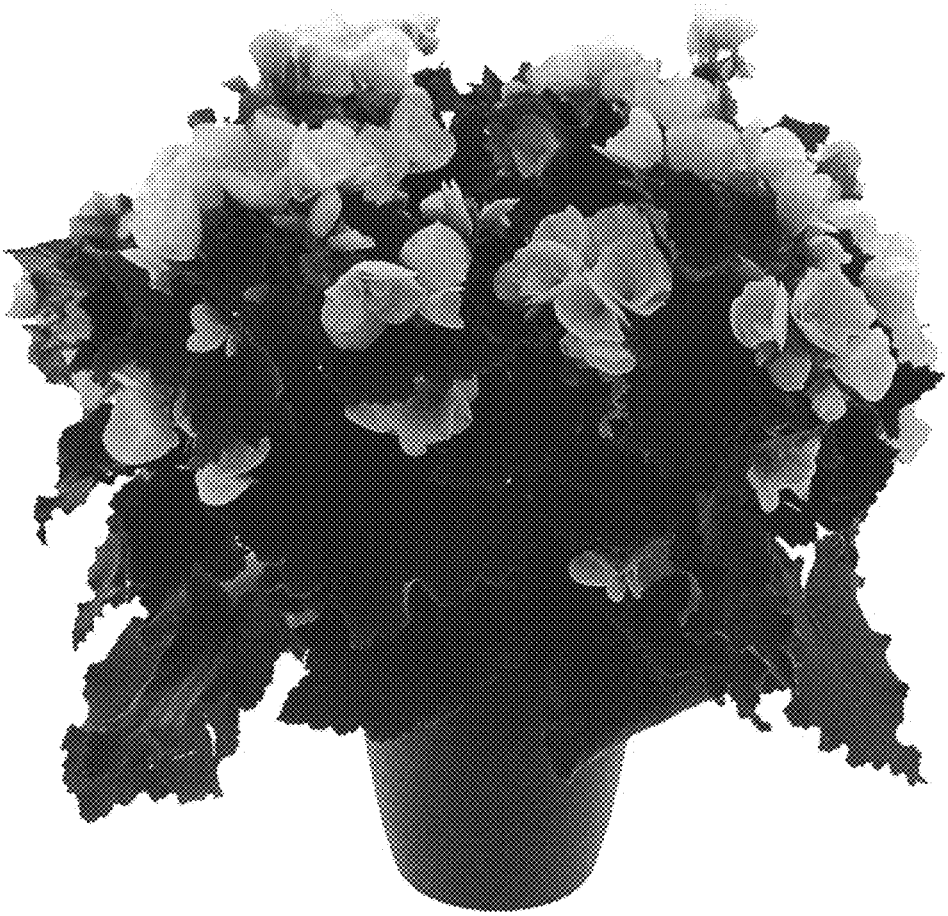

Botanical designation: *Begonia* x *hiemalis*.
Cultivar denomination: 'KRBETWH01'.

STATEMENT REGARDING PRIOR DISCLOSURES BY THE INVENTOR/APPLICANT & ASSIGNEE

An European Community Plant Breeder's Rights application for the instant plant was filed by the Assignee, Koppe Royalty B.V. of Putten, The Netherlands on Nov. 3, 2020, application number 2020/2762. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Begonia* plant, botanically known as *Begonia* x *hiemalis*, commercially referred to as an Elatior *Begonia* and hereinafter referred to by the name 'KRBETWH01'.

The new *Begonia* plant is a product of a planned breeding program conducted by the Inventor in Ermelo, The Netherlands. The objective of the breeding program is to create new freely-branching *Begonia* plants with excellent postproduction longevity and attractive flower color.

The new *Begonia* plant is a naturally-occurring whole plant mutation of *Begonia* x *hiemalis* 'Betulia Bright Pink', disclosed in U.S. Plant Pat. No. 16,842. The new *Begonia* plant was discovered and selected by the Inventor as a single flowering plant from within a population of plants of 'Betulia Bright Pink' in a controlled greenhouse environment in Ermelo, The Netherlands in December, 2017.

Asexual reproduction of the new *Begonia* plant by terminal vegetative cuttings taken in a controlled greenhouse environment in Ermelo, The Netherlands since April, 2018 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRBETWH01'. These characteristics in combination distinguish 'KRBETWH01' as a new and distinct *Begonia* plant:

1. Broadly upright and mounded plant habit.
2. Moderately vigorous to vigorous growth habit.
3. Moderately freely branching habit.
4. Dark green-colored leaves.

5. Freely flowering habit.
6. Semi-double and double-type male flowers that are white in color and held above and beyond the foliar plane.
7. Good postproduction longevity.

Plants of the new *Begonia* differ primarily from plants of the mutation parent, 'Betulia Bright Pink', in flower color as plants of the new *Begonia* have white-colored flowers whereas plants of 'Betulia Bright Pink' have bright red purple-colored flowers.

Plants of the new *Begonia* can be compared to plants of *Begonia* x *hiemalis* 'White Netja', not patented. In side-by-side comparisons conducted in Ermelo, The Netherlands, plants of the new *Begonia* differ primarily from plants of 'White Netja' in plant form as plants of the new *Begonia* are broader and more rounded than plants of 'White Netja'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1) comprises a side perspective view of a typical plant of 'KRBETWH01' grown in a container.

Figure 2:
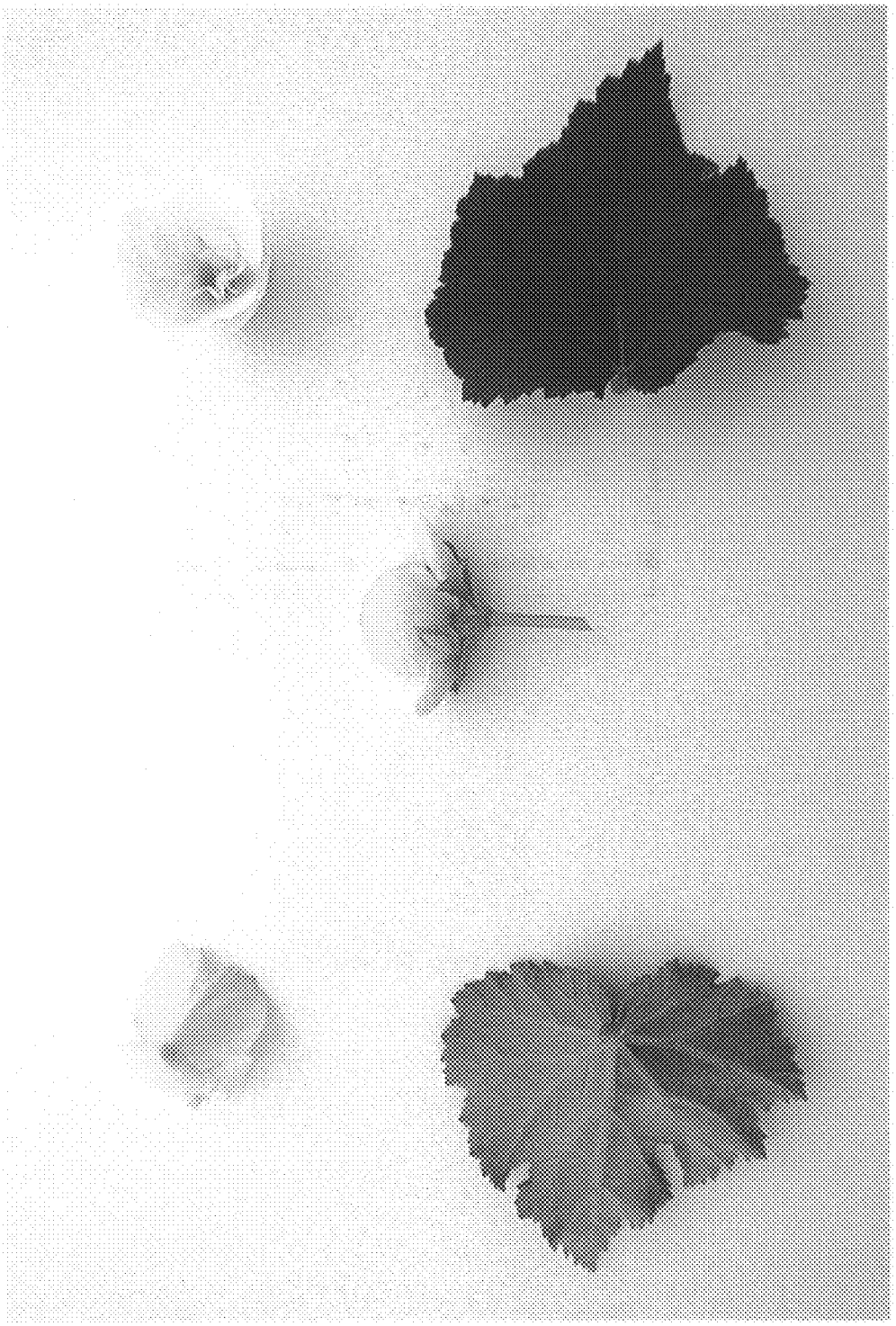

The photograph on the second sheet (FIG. 2) are close up views of the upper (right) and lower (left) surfaces of typical leaves and flowers of 'KRBETWH01', and in the center of the photograph is a close-up view of typical flower buds.

DETAILED BOTANICAL DESCRIPTION

The aforementioned photographs and following observations and measurements describe plants grown during the winter in 11-cm containers in a glass-covered greenhouse in Ermelo, The Netherlands and under cultural practices typical of commercial *Begonia* production. During the production of the plants, day temperatures ranged from 20° C. to 22° C. and night temperatures ranged from 16° C. to 18° C. Plants were three months old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRBETWH01'.

Parentage: Naturally-occurring whole plant mutation of *Begonia* x *hiemalis* 'Betulia Bright Pink', disclosed in U.S. Plant Pat. No. 16,842.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orangish brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Broadly upright and mounded plant habit; overall plant shape, spherical to flattened spherical.

*Growth habit*.—Moderately vigorous to vigorous growth habit and moderate growth rate; suitable for 9-cm and larger containers; under optimal environmental and cultural conditions, usually about eleven weeks from rooted cuttings are required to produce proportional plants in 11-cm containers.

*Branching habit*.—Moderately freely branching with about three primary branches each with about four secondary branches developing per plant.

*Plant height, soil level to top of foliar plane*.—About 27.7 cm.

*Plant height, soil level to top of floral plane*.—About 29.9 cm.

*Plant width*.—About 37.4 cm.

*Lateral branches*.—Length: About 16.3 cm. Diameter: About 8.5 mm to 9 mm. Internode length: About 2.7 cm. Strength: Moderately strong. Aspect: Erect to about 60° from vertical. Texture and luster: Sparsely pubescent; moderately glossy. Color, developing: Close to 146C; surfaces exposed to sunlight are tinged with close to 176C. Color, developed: Close to 179A to 179B tinged with close to 148B to 148C; surfaces exposed to sunlight are darker, close to 178B; at the internodes, close to 178B. Lenticels: None observed on plants of the new *Begonia* to date.

*Leaves*.—Arrangement: Alternate, simple. Length: About 12.4 cm. Width: About 11.2 cm. Shape: Broadly cordate to broadly unequal cordate. Apex: Broadly acute. Base: Cordate to oblique, lobes free and not imbricate. Margin: Crenate to serrate; moderately undulate and slightly crisped. Texture and luster, upper surface: Smooth, glabrous; slightly velvety; slightly glossy. Texture and luster, lower surface: Mostly smooth, glabrous with sparse pubescence along the veins; slightly velvety; moderately glossy. Venation pattern: Pinnate. Color: Developing leaves, upper surface: Close to between NN137A and 147A. Developing leaves, lower surface: Close to 148B. Fully expanded leaves, upper surface: Darker than between 139A and 147A; venation, close to 143A. Fully expanded leaves, lower surface: Close to between 147B and 191A; venation, close to 146A to 146B. Petioles: Length: About 6.8 cm. Diameter: About 5 mm to 6 mm. Strength: Low, flexible. Texture and luster, upper and lower surfaces: Sparsely pubescent; moderately glossy. Color, upper surface: Close to 176A; distally, strongly tinged with close to 178A. Color, lower surface: Close to 176B; distally, strongly tinged with close to 183B. Stipules: Quantity and appearance: Two leafy stipules at the base of each leaf. Length: About 1 cm. Width: About 7 mm. Shape: Broadly ovate. Apex: Broadly acute. Base: Broadly cuneate. Margin: Finely ciliate. Color, upper and lower surfaces: Close to 146D to lighter than 146D.

Flower description:

*Flower form and flowering habit*.—Single and double-type male rotate flowers arranged in axillary cymes;

to date, female flower development has not been observed on plants of the new *Begonia*; typically about nine flowers per cyme, numerous cymes in flower simultaneously and about 675 flowers developing per plant; flowers face upright to outwardly and are positioned above and beyond the foliar plane.

*Natural flowering season*.—Plants flower continuously from the spring into the autumn in The Netherlands; plants begin flowering about five weeks after pinching.

*Flower longevity*.—Individual flowers last about ten days on the plant; flowers not persistent.

*Fragrance*.—None detected.

*Inflorescence height*.—About 11 cm.

*Inflorescence diameter*.—About 8.7 cm.

*Flower buds*.—Length: About 1.4 cm. Diameter: Ranging from about 6 mm to 17 mm. Shape: Obovate, flattened. Texture and luster: Smooth, glabrous; velvety; matte. Color: Close to between 145D and 150D.

*Male flowers*.—Diameter: About 3.4 cm. Depth: About 2.6 cm. Tepals: Quantity and arrangement: About four arranged in two whorls. Length, inner whorl tepals: About 2.5 cm. Length, outer whorl tepals: About 3 cm. Width, inner whorl tepals: About 2.8 cm. Width, outer whorl tepals: About 3 cm. Shape: Broadly obovate to roughly orbicular. Apex: Mostly rounded. Base: Truncate. Margin: Entire, not undulate. Texture and luster, upper surface: Smooth, glabrous; moderately velvety; matte. Texture and luster, lower surface: Smooth, glabrous; slightly velvety; slightly glossy. Color, inner whorl tepals: When opening and fully opened, upper surface: Close to between 155C and 157D; venation, close to 157A; color does not change with subsequent development. When opening, lower surface: Close to between 155C and 157D; towards the base, close to 157D; venation, close to 157A; color does not change with subsequent development. Color, outer whorl tepals: When opening and fully opened, upper surface: Close to 157C; venation, close to 157A; with subsequent development, color becoming closer to 157A, towards the base, close to 145B and distally tinged with close to 41D to lighter than 41D. When opening, lower surface: Close to 157A to 157B; towards the base, close to between 145D and 157A; venation, close to 157A; with subsequent development, color becoming closer to 145D, towards the base, close to 145B and distally tinged with close to 41D. Tepaloids: Quantity and arrangement per flower: Variable, up to 15 per flower arranged in up to four whorls. Length: About 3 mm to 24 mm. Width: About 2.5 mm to 23 mm. Shape: Obovate to obcordate. Apex: Obtuse to retuse. Base: Cuneate to attenuate. Margin: Entire; not undulate. Texture and luster, upper surface: Smooth, glabrous; velvety; matte. Texture and luster, lower surface: Smooth, glabrous; moderately velvety; matte. Color: When opening, upper surface: Close to 157B; towards the base, close to 145C to 145D. When opening, lower surface: Close to 145D; towards the base, close to 145C. Fully opened, upper and lower surfaces: Close to 155C; towards the base, close to 145C; venation, similar to lamina color; color does not change with subsequent development.

*Flower bracts*.—Quantity and arrangement: Two positioned at the top of the peduncle. Length: About 1.5 cm. Width: About 1.3 cm. Shape: Broadly ovate. Apex: Praemorse. Base: Broadly cuneate. Margin: Finely ciliate. Texture and luster, upper and lower surfaces: Smooth, glabrous; slightly glossy. Color, upper and lower surfaces: Close to 145A; venation, close to 143B.

*Peduncles*.—Length: About 4.2 cm. Diameter: About 3.5 mm to 4.5 mm. Strength: Moderately strong. Aspect: About 45° from lateral branch axis. Texture and luster: Sparsely pubescent; glossy. Color: Close to 146C to 146D; proximally, tinged with close to 184A.

*Pedicels*.—Length: About 1.6 cm. Diameter: About 2 mm. Strength: Moderately strong. Aspect: About 30° from peduncle axis. Texture and luster: Moderately pubescent; moderately glossy. Color: Close to 144A.

*Reproductive organs*.—Stamens (present on male flowers only): No stamens observed as all stamens transformed into tepaloids. Pistils (present on female flowers only): To date, no female flower development has been observed on plants of the new *Begonia*. Seeds and fruits: To date, seed and fruit development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures about 35° C. and to be suitable for USDA Hardiness Zones 10 to 12.

It is claimed:

1. A new and distinct *Begonia* plant named 'KRBETWH01' as illustrated and described.

* * * * *